(12) United States Patent
Zhang

(10) Patent No.: US 8,318,942 B2
(45) Date of Patent: Nov. 27, 2012

(54) PROCESS FOR PREPARING DONEPEZIL AND ITS DERIVATIVES

(75) Inventor: Heshang Zhang, Tianjin (CN)

(73) Assignee: Tianjin Hemay Bio-Tech Co., Ltd., Tianjin (CN)

( * ) Notice: Subject to any disclaimer, the term of this patent is extended or adjusted under 35 U.S.C. 154(b) by 1272 days.

(21) Appl. No.: 10/595,609

(22) PCT Filed: Oct. 28, 2004

(86) PCT No.: PCT/CN2004/001227
§ 371 (c)(1),
(2), (4) Date: Apr. 30, 2006

(87) PCT Pub. No.: WO2005/044805
PCT Pub. Date: May 19, 2005

(65) Prior Publication Data
US 2007/0072905 A1    Mar. 29, 2007

(30) Foreign Application Priority Data
Nov. 5, 2003 (CN) .......................... 2003 1 0106920

(51) Int. Cl.
*C07D 311/32* (2006.01)

(52) U.S. Cl. ......... 546/206; 546/205; 546/238; 546/324

(58) Field of Classification Search ................... 546/205, 546/206, 238, 324
See application file for complete search history.

(56) References Cited

U.S. PATENT DOCUMENTS

| | | | |
|---|---|---|---|
| 5,606,064 A | 2/1997 | Lensky | |
| 5,916,902 A * | 6/1999 | Devries et al. | 514/321 |
| 7,148,354 B2 * | 12/2006 | Reddy et al. | 546/206 |

FOREIGN PATENT DOCUMENTS

| | | |
|---|---|---|
| EP | 0 296 560 A2 | 12/1988 |
| EP | 0 535 496 A1 | 7/1993 |
| WO | 97/22584 A1 | 6/1997 |
| WO | 99/36405 A1 | 7/1999 |
| WO | WO2004/082685 * | 9/2004 |

OTHER PUBLICATIONS

Sugimoto et al. "Preparation of . . . " CA 110:173102 (1989).*
Sugimoto et al. "Preparation of piperidine . . . " CA 114:6302 (1991).*
Bobbitt et al."Steric requirement . . . " CA 69:402372 (1968).*
Morison & Boyd "Organic chemistry" p. 397-398 (1973).*
Ranbaxy Lab. "Priority document for PCT/IB2004/000843" (2003).*

* cited by examiner

*Primary Examiner* — Celia Chang
(74) *Attorney, Agent, or Firm* — Matthias Scholl P.C.; Matthias Scholl

(57) ABSTRACT

A process for producing a Donepezil derivative represented by the formula (I), wherein $R^1$, $R^2$, $R^3$, and $R^4$ each independently represents H, F, an alkyl having from 1 to 4 carbon atoms, or an alkoxy having from 1 to 4 carbon atoms; $R^5$ represents a phenyl or a substituted phenyl; and n is an integer from 0 to 2, characterized in that the process comprises: (a) a reaction of 4-pyridinecarboxaldehyde with a compound of formula (II) in the presence of a strong acid HX to form a compound of formula (III); (b) a catalytic hydrogenation of a compound of formula (III) or a compound of formula (V) to yield a compound of formula (IV); and (c) an alkylation reaction of a compound of formula (IV) to yield a compound of formula (I).

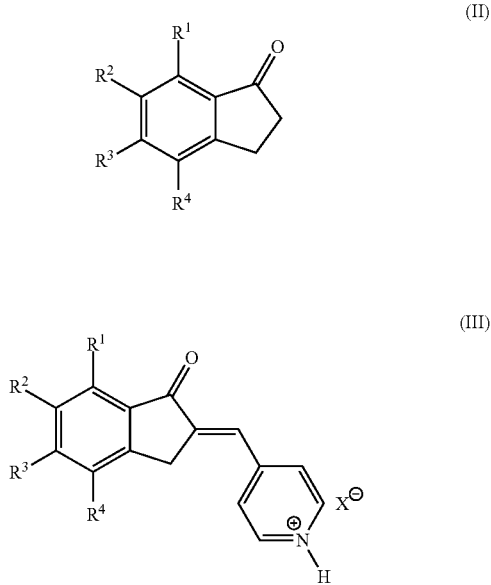
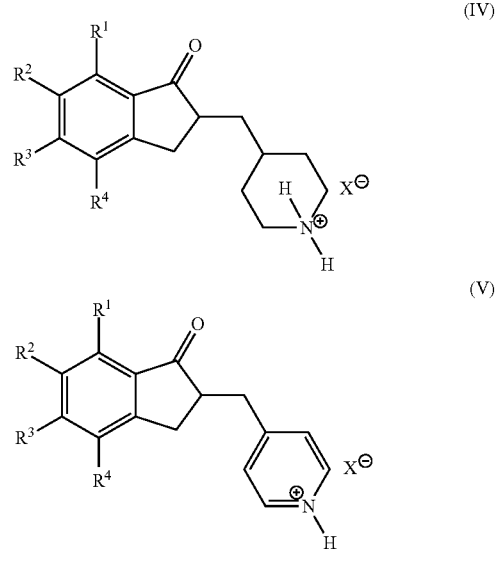
21 Claims, 4 Drawing Sheets

PROCESS FOR PREPARING DONEPEZIL AND ITS DERIVATIVES

CROSS-REFERENCE TO RELATED APPLICATIONS

This is a National Stage Application of International Patent Application No. PCT/CN 2004/001227, with an international filing date of Oct. 28, 2004, which is based on Chinese Patent Application No. 200310106920.3, filed Nov. 5, 2003. The contents of both of these specifications are incorporated herein by reference.

FIELD OF THE INVENTION

This invention relates to novel synthesis of Donepezil and derivatives thereof.

BACKGROUND OF THE INVENTION

Donepezil is an acetyl cholinesterase inhibitor exhibiting high selectivity, high bioavailability, and high potency. It is able to inhibit acetyl cholinesterase present in the brain while only slightly effecting acetylcholine levels present in other tissues, such as the myocardium and the erythrocytes specifically. Other advantages of using Donepezil include its persistent activity and good safety profile. In addition, patients taking Donepezil have good tolerance for the drug. Since Donepezil demonstrated good efficacy in the treatment of Alzheimer senile dementia, it is a very valuable drug with growing market share. Accordingly, Donepezil and its derivatives is a hot synthetic target.

The synthesis of Donepezil was first disclosed by Japan's Eisai Co. in the U.S. Pat. No. 5,100,901 (see FIG. 1 herein), with an overall yield of less than 20%.

EPO Patent EP 535496 then disclosed an economically viable scheme for the synthesis of Donepezil (see FIG. 2 herein). However, this synthetic route resulted in many by-products in the first step, and required complicated purification procedures, such as column chromatography. We have found similar problems when we attempted to repeat this process. In addition, this process was difficult to reproduce. Therefore, it inevitably lead to complex purification procedure and a poor overall yield of 29 percent (see FIG. 2 herein). We predict that this process would be difficult to employ on an industrial scale. There are no continued patent applications of EP 535496 so far.

The German Company Bayer disclosed yet another process for the production of Donepezil in the U.S. Pat. No. 5,606,064 (see FIG. 3 herein). This process consists of 2 steps. The overall yield of this process is reported as 53%. However, when scientists of Eisai Co. attempted to repeat this process, they had found that the yield for the key step, step 2, was actually only 38% (U.S. Pat. No. 6,252,081). Therefore, the total yield of the Bayer process could not have been more than 27% overall.

Recently, Eisai Co. disclosed in the U.S. Pat. No. 6,252,081 an improved route for the preparation of Donepezil (see FIG. 4 herein). This route calls for recrystallization at each step, and the yield in the key step (last step) is high, while the by-products in that step are few. Hence, this route is the most efficient process at present, with a 69% overall yield. However, this route utilizes NaH in two steps, a high concentration NaOH solution in one step, and requires absolute dry solvents in two steps. As such, the route utilizes complicated operating parameters in each step, necessitating large investment for equipment, such as moisture proof equipment and caustic resistant equipment.

Finetech also developed two novel processes (U.S. Pat. No. 6,252,081; see FIGS. 5 and 6 herein). The yield of the process as illustrated in FIG. 5 was not disclosed, and the process required complicated purification techniques and column chromatography in many of its steps. Therefore, this process is not deemed suitable as an industrial process.

Although the synthesis, disclosed in FIG. 6 herein, requires multiple steps, it employs purification by recrystallization and distillation rather than by column chromatography in each step; this renders the industrialization of the process possible. It is said that the process was successfully employed in a pilot plant. However, this process also requires complicated operating parameters in each step, and utilizes strong acid and caustic reagents in multiple steps, generating a lot of waste. This process requires many complicated steps, and although the yields of each step are high, the overall yield was a mere 19.3% (see FIG. 6 herein). For these reasons, the commercial value of the process is limited.

In sum, there were 6 previously disclosed processes for the preparation of Donepezil and its derivatives. Wherein the process in FIG. 1 (herein) is an industrial one, processes in FIGS. 4 and 6 succeeded in a pilot plant. There is no continued patent application of the process in FIG. 6 (herein) after its EP application. There is also no successful report of a pilot plant of the process in FIG. 3 (herein).

The processes in FIGS. 2 and 3 have the shortest synthetic route. With respect to the results of the synthetic scheme illustrated herein in FIG. 2 which we have repeated, because the 2,3-dihydro-5,6-dimethoxy-2-((pyridin-4-yl)methylene) inden-1-one is a conjugated system, it is difficult to hydrogenate the pyridine ring and the carbon-carbon double bond at the same time in the presence of a catalyst. If hydrogenation is performed at an elevated temperature and pressure, the carbonyl group may also be reduced to a hydroxyl group making the purification more difficult, and yielding less than 40% of the desired material after purification by column chromatography. Moreover, the process illustrated herein in FIG. 3 also causes trouble in the same step of catalytic hydrogenation; although the N-benzylization on the pyridine ring can form a quaternary pyridinium salt, which makes the pyridine ring more active towards hydrogenation, the benzyl group is easily broken up by hydrogenolysis under these conditions as well. The results obtained by Eisai Co. and those obtained in our laboratory show that this reaction has many by-products, which makes the purification difficult, and the yields low.

There are two methods to solve the aforesaid problems, one is to use the synthetic scheme Eisai Co. developed as shown herein in FIG. 4: the pyridine analogues obtained from this process are not conjugated with the indanone ring; the pyridine ring can be activated through forming quaternary pyridinium salt; and as a result, the pyridine ring in the form of the N-benzyl quaternary pyridinium salt can be hydrogenated under mild reaction conditions. Consequently, the final products are obtained in higher yields.

The other method is to activate the pyridine ring by forming quaternary methyl ammonium salts rather than quaternary benzyl ammonium salts, and in this way to avoid the side reactions in the presence of a hydrogenation catalyst, as in the process disclosed by Joseph Sam (*J. Hetercyclo. Chem.* Vol. 2, 366; FIG. 7 herein). However, although the yield of this process is said to be 100%, this process is not suitable for the preparation of Donepezil.

SUMMARY OF THE INVENTION

To overcome the disadvantages of the synthetic schemes illustrated in FIGS. 2 and 3, we have tried to activate the pyridine ring in the absence of side reactions. Using as a guide the reaction illustrated in FIG. 7, we attempted forming an activated pyridinium salt via protonating the nitrogen atom of the pyridine ring of 2,3-dihydro-2-((pyridin-4-yl)methylene)inden-1-ones with a strong acid. The conjugated pyridinium ring could be easily hydrogenated in the presence of a catalyst to form a

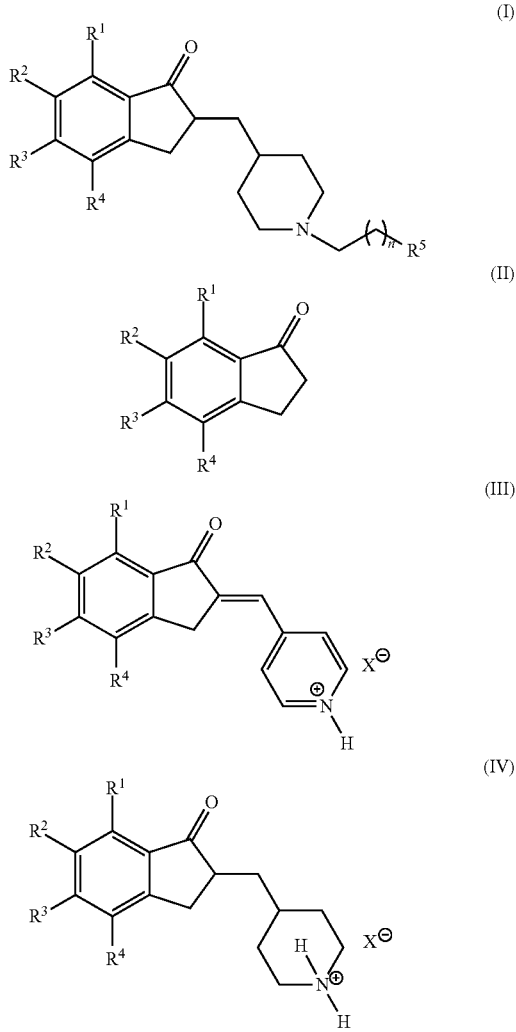

protonated piperidinium salt (represented by formula (IV) below), and to afford Donepezil and its derivatives (see FIG. 8 herein). In this way, not only the compounds of formula (IV) could be afforded in high yields through the hydrogenation of the pyridine ring of the compounds of formula (III) in the presence of a catalyst under mild reaction conditions, but also the compounds of formula (IV) could be converted to the target compounds easily by alkylation processes.

Accordingly, the invention relates to a process for producing of compounds represented by the following formula (I), wherein $R^1$, $R^2$, $R^3$, and $R^4$ each independently represents H, F, an alkyl having from 1 to 4 carbon atoms, or an alkoxy having 1 to 4 carbon atoms; $R^5$ represents phenyl or substituted phenyl; and n is an integer from 0 to 2, characterized in that, the process comprises the following three reactions represented in FIG. 8 below:

Step one is the reaction of 4-pyridinecarboxaldehyde with a compound of the formula (II) to form a compound of the formula (III) in the presence of a strong acid, wherein $R^1$, $R^2$, $R^3$, and $R^4$ each independently represents H, F, an alkyl having from 1 to 4 carbon atoms, or an alkoxy having from 1 to 4 carbon atoms. The term "HX" refers to a strong acid which could stabilize the compound of the formula (III), including but not limited to alkyl sulfonic acid, benzene sulfonic acid, substituted benzene sulfonic acid, terephthalic sulfonic acid, hydrochloric acid, sulfuric acid, nitric acid, phosphoric acid, 1-naphthalenesulfonic acid, and 2-naphthalenesulfonic acid. Preferred acids include methyl sulfonic acid, ethyl sulfonic acid, benzene sulfonic acid, p-toluene sulfonic acid, terephthalic sulfonic acid, 1-naphthalenesulfonic acid, 2-naphthalenesulfonic acid, sulfuric acid, and phosphoric acid. More preferred acids include methyl sulfonic acid, benzene sulfonic acid and p-toluenesulfonic acid.

Second step is the reaction of a compound of the formula (III) with $H_2$ in the presence of a catalyst to form the compound of the formula (IV), wherein $R^1$, $R^2$, $R^3$, and $R^4$ each independently represents H, F, an alkyl having from 1 to 4 carbon atoms, or an alkoxy having from 1 to 4 carbon atoms. The term "HX" refers to a strong acid which could stabilize the compound of the formula (III), including but not limited to alkyl sulfonic acid, benzene sulfonic acid, substituted benzene sulfonic acid, terephthalic sulfonic acid, hydrochloric acid, sulfuric acid, nitric acid, phosphoric acid, 1-naphthalenesulfonic acid, or 2-naphthalenesulfonic acid. Preferred acids include methyl sulfonic acid, ethyl sulfonic acid, benzene sulfonic acid, p-toluene sulfonic acid, terephthalic sulfonic acid, 1-naphthalenesulfonic acid, 2-naphthalenesulfonic acid, sulfuric acid, and phosphoric acid. More preferred acids include methyl sulfonic acid, benzene sulfonic acid, and p-toluene sulfonic acid.

A compound of the formula (IV) could be produced by the reaction of a compound of the formula (V) with $H_2$ in the presence of a catalyst, wherein $R^1$, $R^2$, $R^3$, and $R^4$ each independently represents H, F, an alkyl having from 1 to 4 carbon atoms, or an alkoxy having from 1 to 4 carbon atoms. The term "HX" refers to a strong acid which could stabilize the compound of the formula (III), including but not limited to alkyl sulfonic acid, benzene sulfonic acid, substituted benzene sulfonic acid, hydrochloric acid, sulfuric acid, nitric acid, phosphoric acid, 1-naphthalenesulfonic acid, and 2-naphthalene sulfonic acid. Preferred acids include methyl sulfonic acid, ethyl sulfonic acid, benzene sulfonic acid, p-toluene sulfonic acid, 1-naphthalenesulfonic acid, 2-naphthalenesulfonic acid, sulfuric acid, nitric acid, and phosphoric acid. More preferable acids include methyl sulfonic acid, benzene sulfonic acid, and p-toluene sulfonic acid.

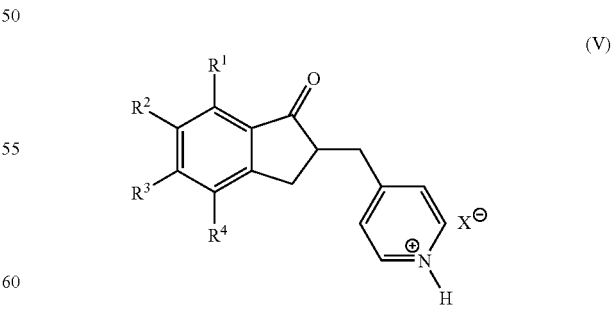

Examples of catalysts used in the hydrogenation reactions in which a compound of formula (IV) is produced from a compound of formula (III) or in which a compound of formula (V) reacts with $H_2$ include platinum, palladium, rhodium, nickel, ruthenium, and also oxides or salts thereof.

Preferred are palladium on carbon, platinum on carbon, Raney nickel, platinum dioxide, platinum chloride, and palladium chloride. More preferred is platinum dioxide.

The reaction can be carried out in a pressure range from about 1 atmosphere to about 100 atmospheres of $H_2$, preferably from about 1 to about 20 atmospheres, and more preferably from about 1 to about 5 atmospheres. The reaction generally is carried out in a temperature range from about 0 degrees Celsius to about +150 degrees Celsius, preferably from about +10 degrees Celsius to about +100 degrees Celsius, and more preferably from room temperature to about +50 degrees Celsius.

The ratio of a reactant, for example of a compound of formula (III) or formula (V) to a catalyst is from 1:0.001 to 1:0.5, and preferably from 1:0.01 to 1:0.2. A suitable solvent in this reaction may be selected from, but is not limited to, water, an alcohol, an ether, an ester, or an organic acid; preferably water, methanol, ethanol, propanol, isopropanol, tetrahydrofuran, ethyl acetate, or acetic acid; and more preferably water, methanol, ethanol, tetrahydrofuran, or acetic acid.

The third step is the reaction of $Y-(CH_2)_{n+1}R^5$ with a compound of formula (IV) in the presence of a base to give a compound of formula (I), wherein $R^1$, $R^2$, $R^3$ and $R^4$ each independently represents H, F, an alkyl having from 1 to 4 carbon atoms, or an alkoxy having from 1 to 4 carbon atoms; $R^5$ represents a phenyl or a substituted phenyl; n is an integer from 0 to 2; and Y is a chlorine atom, a bromine atom, or an iodine atom.

Said base is an organic base or an inorganic base; preferably $K_2CO_3$, $Cs_2CO_3$, $Na_2CO_3$, $KHCO_3$, $NaHCO_3$, $CaCO_3$, $Ca(OH)_2$, $Li_2CO_3$, $K_3PO_4$, $Na_3PO_4$, $K_2HPO_4$, or $Na_2HPO_4$; and more preferably $K_2CO_3$, $Cs_2CO_3$ or $Na_2CO_3$.

The molar ratio of a compound of formula (IV) to a compound of formula $YCH_2(CH_2)_nR^5$ ranges from 1:0.3 to 1:3. The molar ratio of a compound of formula (IV) to a base ranges from 1:0.3 to 1:50. More preferably the ratio of a compound of formula (IV) to a compound of formula $YCH_2(CH_2)_nR^5$ to a base is 1 to 0.8-1.5 to 0.8-2.

Examples of solvents used in this reaction include N,N-dimethylformamide, N,N-dimethylacetamide, acetonitrile, tetrahydrofuran, dichloromethane, trichloromethane, 1,2-dichloroethane, 1,4-dioxane, ethyl acetate, isopropanol, isopropyl ether, acetone, 2-butanone, HMPA, and dimethylsulfoxide; preferably, N,N-dimethylformamide, N,N-dimethylacetamide, acetonitrile, dichloromethane, 1,2-dichloroethane, tetrahydrofuran, dimethyl sulfoxide, acetone, and ethyl acetate; and more preferably, N,N-dimethylformamide, N,N-dimethylacetamide, acetonitrile, dichloromethane, 1,2-dichloroethane, tetrahydrofuran, and dimethyl sulfoxide. The reaction is in general carried out in a temperature range from 0 degrees Celsius to +150 degrees Celsius; preferably, from 10 degrees Celsius to +100 degrees Celsius; and more preferably from room temperature to +50 degrees Celsius.

Another method for the preparation of a compound of formula (I) is the reaction of $OHC-(CH_2)_nR^5$ with a compound of formula (IV) and $H_2$, in the presence of a catalyst. The catalyst is platinum, palladium, nickel, rhodium, or ruthenium, or salts or oxides thereof. Preferably the catalyst is palladium on carbon, platinum on carbon, platinum dioxide, palladium chloride, platinum chloride, or Raney nickel. More preferably the catalyst is palladium on carbon. $H_2$ can be supplied at a pressure range from 1 to 100 atmospheres; and preferably at a pressure from 1 to 5 atmospheres. Adding a weak-acids salt such as sodium acetate, and potassium acetate will improve the reaction. The reaction is in general carried out in a temperature range from 0 degrees Celsius to +150 degrees Celsius; preferably, from 10 degrees Celsius to +100 degree Celsius; and more preferably from room temperature to +50 degrees Celsius.

The molar ratio of a compound of formula (IV) to a compound of formula $OHC(CH_2)_nR^5$ to a catalyst is 1 to 0.5-3 to 0.001-0.5. Preferably, the molar ratio of a compound of formula (IV) to a compound of formula $OHC(CH_2)_nR^5$ to a catalyst is 1 to 0.8-1.5 to 0.01-0.2. The solvent in this reaction may be selected from water, dichloromethane, chloroform, 1,4-dioxane, an alcohol, an ether, an ester, or an organic acid; preferably from, water, methanol, ethanol, propanol, isopropanol, dichloromethane, chloroform, 1,4-dioxane, tetrahydrofuran, ethyl acetate, or acetic acid; and more preferably from, tetrahydrofuran, dichloromethane, chloroform, or 1,4-dioxane.

The third method for preparation of a compound of formula (I) is the reaction of a compound of formula $OHC-(CH_2)_nR^5$ with a compound of formula (IV) and a reducing agent, wherein the reducing agent is selected from, but not limited to, $NaBH_4$, $B_2H_6$, $NaBH(CN)_3$, $NaBH(AcO)_3$, and $Ca(BH_4)_2$. The molar ratio of a compound of formula (IV) to a compound of formula $OHC(CH_2)_nR^5$ to a reducing agent is 1 to 0.5-3 to 0.5-4. Preferably, the molar ratio of a compound of formula (IV) to a compound of formula $OHC(CH_2)_nR^5$ to a reducing agent is 1 to 0.8-1.5 to 0.8-1.5. The solvent in this reaction is selected from, but not limited to, tetrahydrofuran, dichloromethane, trichloromethane, ethyl acetate, 1,4-dioxane, 1,2-dichloroethane, isopropanol, isopropyl ether, and acetic acid; and preferably, tetrahydrofuran dichloromethane, trichloromethane, ethyl acetate, 1,4-dioxane, 1,2-dichloroethane and acetic acid. The reaction is in general carried out in a temperature range from 0 degrees Celsius to +100 degrees Celsius; and more preferably, from room temperature to +60 degrees Celsius.

Compounds which are suitable to be used as an active pharmaceutical ingredient in therapeutic compositions and suitable to be produced by methods of this invention are compounds represented by formula (I), wherein $R^1$, $R^2$, $R^3$, and $R^4$ each independently represent H, F, Me, OMe or OEt; preferably, $R^1$ and $R^4$ each independently represent H, or F; $R^2$ and $R^3$ each independently represent OMe or OEt; more preferably, $R^1$ and $R^4$ each represent H; and $R^2$ and $R^3$ each represent OMe.

Compounds which are suitable to be used as an active pharmaceutical ingredient in therapeutic compositions and suitable to be produced by methods of this invention are compounds represented by formula (I), wherein $R^5$ represents phenyl or substituted phenyl; preferably, $R^5$ represents phenyl, 3-chloropropylphenyl, 3-bromomethylphenyl, 3-methoxyphenyl, 2-fluorophenyl, 3-fluorophenyl, or 4-fluorophenyl; and more particularly, $R^5$ represents phenyl or 3-fluorophenyl.

Compounds which are suitable to be used as an active pharmaceutical ingredient in therapeutic compositions and suitable to be produced by methods of this invention are compounds represented by formula (I), wherein n is an integer from 0 to 2; preferably, n is 0 or 1; and more preferably, n is 0.

More preferably, compounds which are suitable to be used as an active pharmaceutical ingredient in therapeutic compositions and suitable to be produced by methods of this invention are compounds represented by formula (I), wherein $R^1$ and $R^4$ each represent H; $R^2$ and $R^3$ each represent OMe; $R^5$ represents phenyl or 3-fluorophenyl; and n is 0.

In certain embodiments, the invention shows advantages as explained in detail with reference to examples describing synthesis of Donepezil, wherein $R^1$ represents hydrogen, $R^2$ represents OMe, $R^3$ represents $OCH_3$, $R^4$ represents hydrogen, $R^5$ represents phenyl, and n is 0.

The addition of the 4-pyridylmethylene moiety to the compound of formula (II) (wherein $R^1$ represents hydrogen, $R^2$ represents OMe, $R^3$ represents $OCH_3$, and $R^4$ represents hydrogen) is described below. Specifically, the reaction of 4-pyridinecarboxaldehyde with a compound of formula (II) in the presence of p-toluenesulfonic acid under reflux conditions in the toluene as solvent results after cooling in a brown crystalline compound of formula (III). The product is obtained in a high yield of 91%. The purity of this product is greater than 98%. In addition, we have found that compounds of formula (IV) can be obtained by reacting a compound of formula (III) with $H_2$ in the presence of a catalyst, such as platinum dioxide. $H_2$ is supplied at 1 atmosphere of pressure and room temperature. The resulted reduced p-toluene-sulfonic acid salt (IV) is converted to Donepezil by the reaction with benzyl bromide. Therefore, the total yield of the Donepezil route according to this invention is as high as 82%.

Accordingly, the invention affords a process for the preparation of Donepezil and derivatives thereof, which compared with prior techniques, demonstrates the advantage of mild reaction conditions, easy operation and control, and little waste.

The implementation of syntheses of this invention can reduce the cost of producing Donepezil, improve product economics, and decrease pollution.

DETAILED DESCRIPTION OF THE INVENTION

Examples

Example 1

Figure 1:
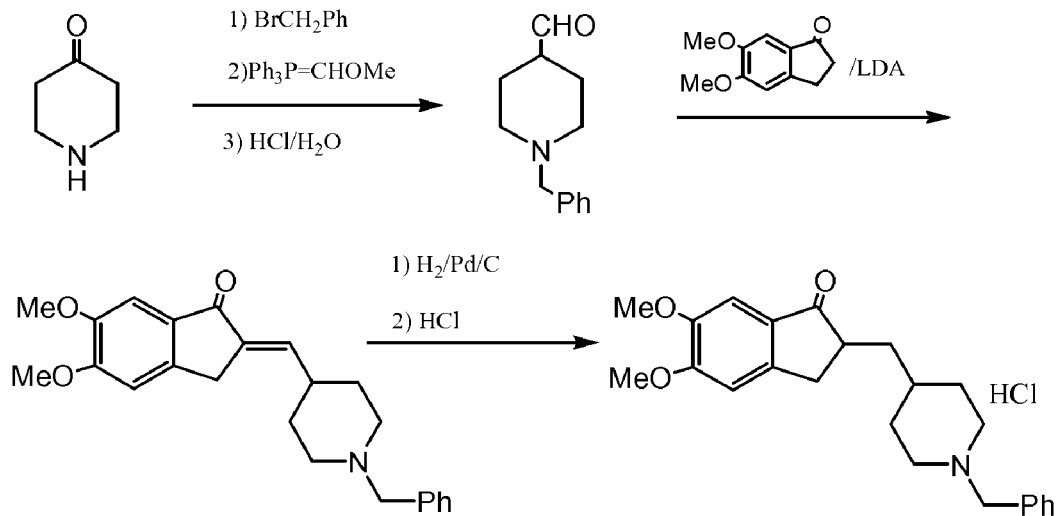
FIG. 1 illustrates a process for the preparation of Donepezil by Japan's Eisai Company.
Figure 2:
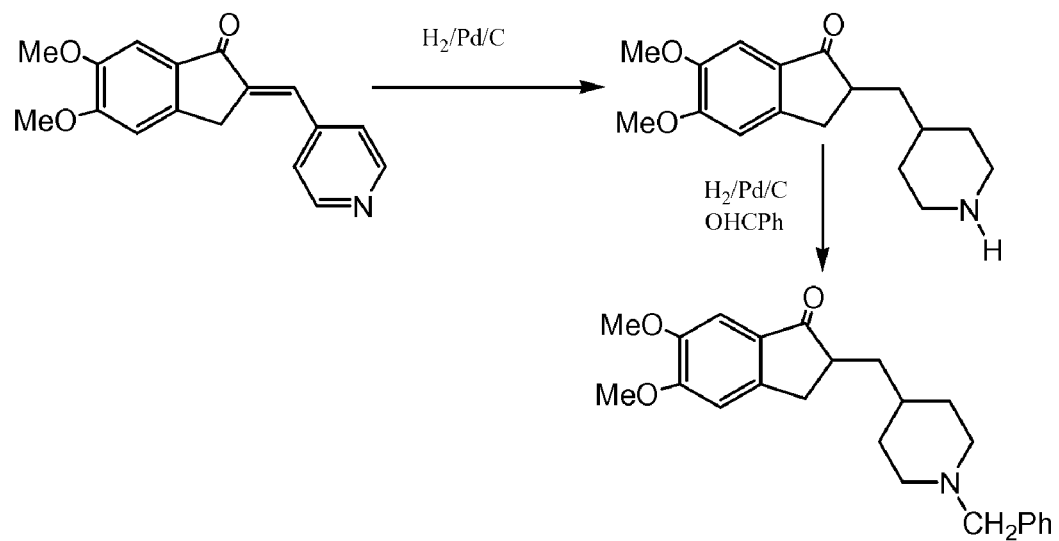
FIG. 2 illustrates a process for the preparation of Donepezil as disclosed in European Patent Application EP535496.
Figure 3:
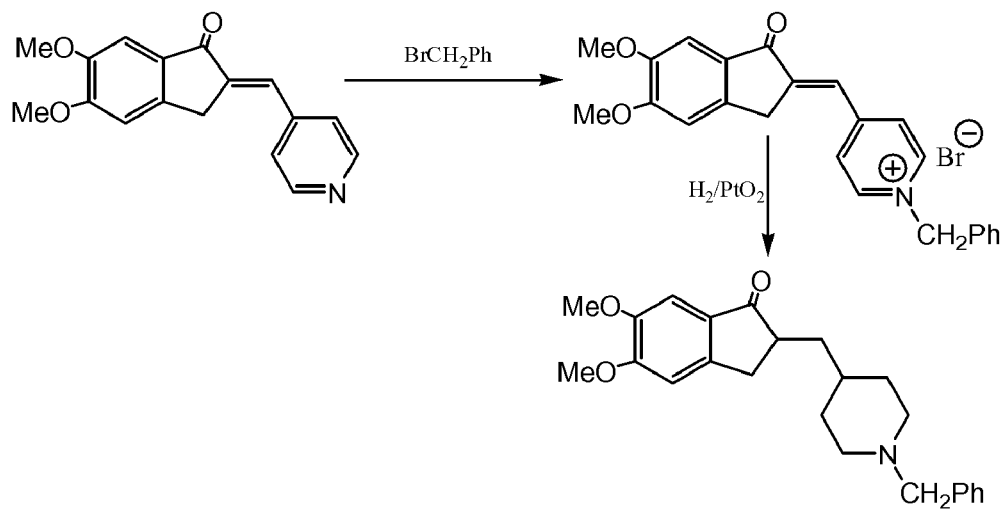
FIG. 3 illustrates a process for the preparation of Donepezil by the German company Bayer.
Figure 4:
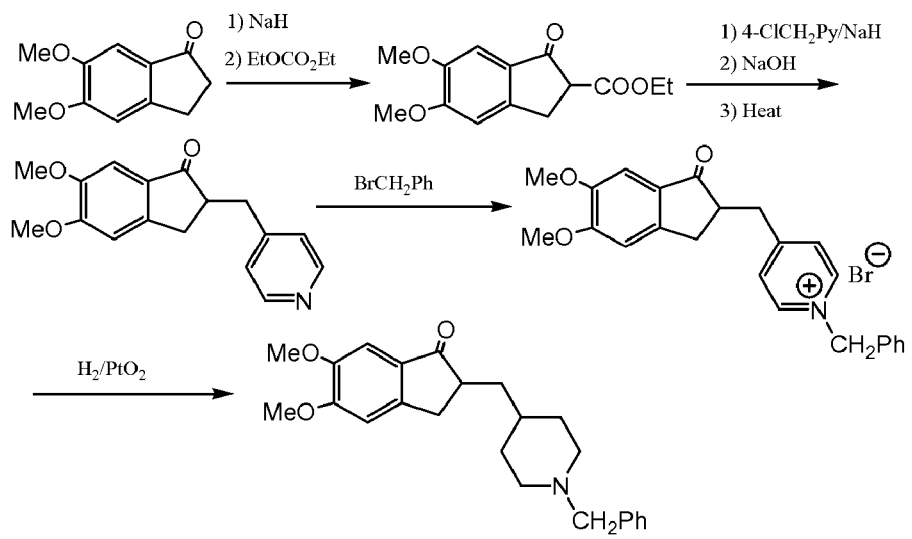
FIG. 4 illustrates an improved process for the preparation of Donepezil by Japan's Eisai Co.
Figure 5:
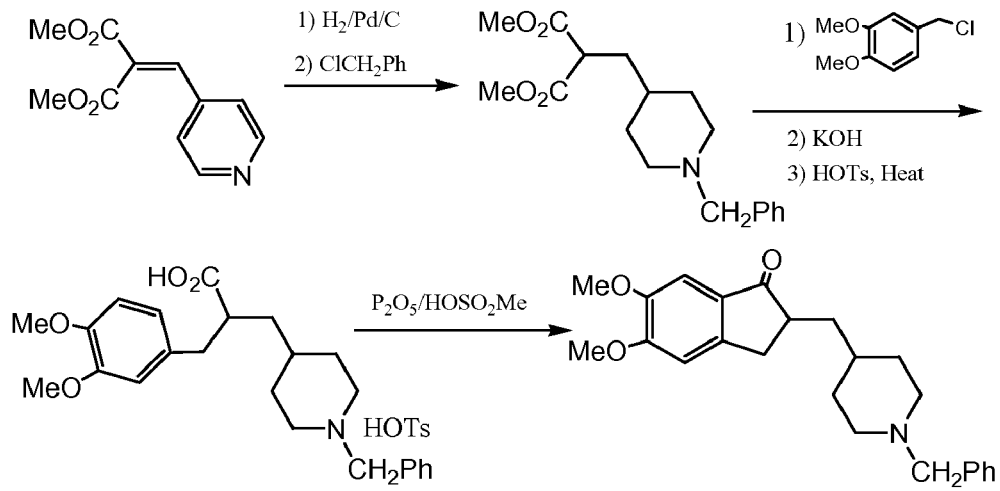
FIG. 5 and FIG. 6 illustrate a process for the preparation of Donepezil by Finetech.
Figure 6:
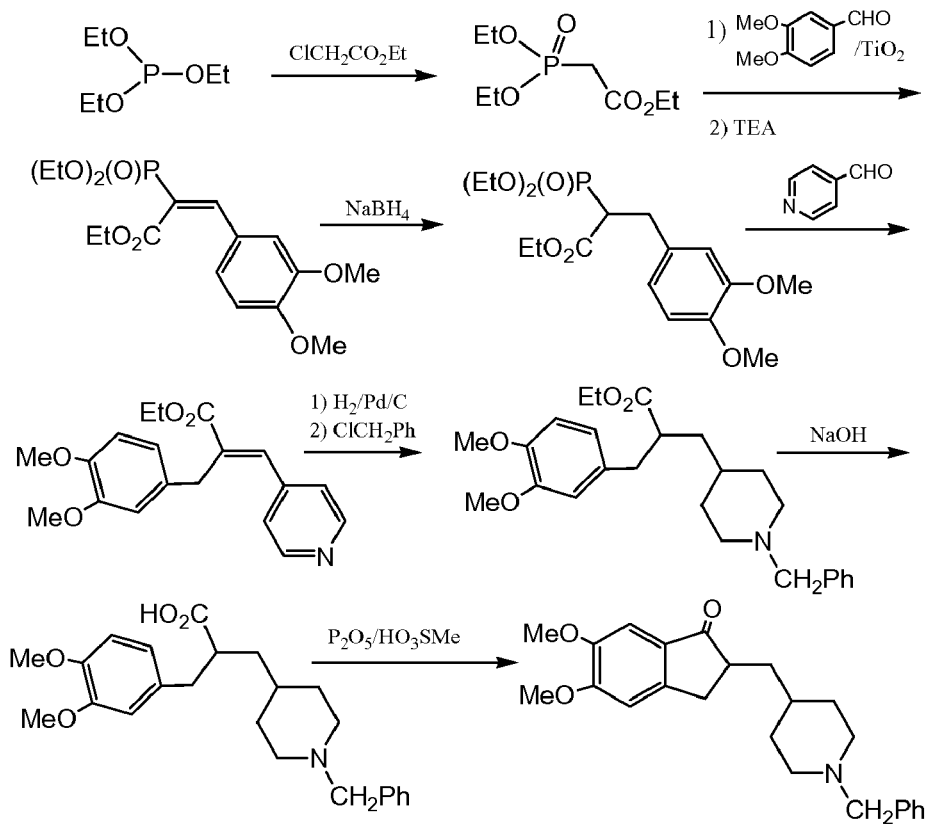
Figure 7:
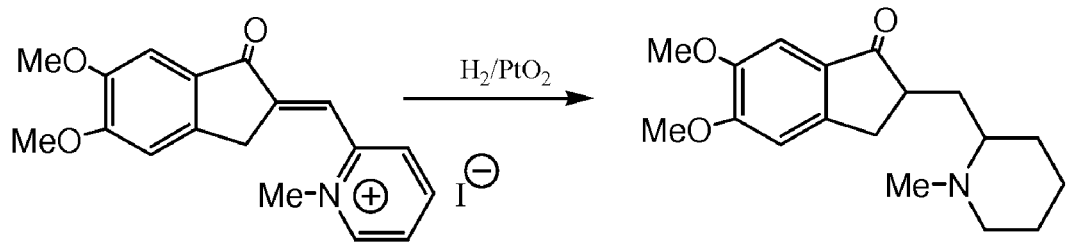
FIG. 7 illustrates the hydrogenation of the N-methyl quaternary pyridine ammonium salt in the presence of a hydrogenation catalyst.
Figure 8:
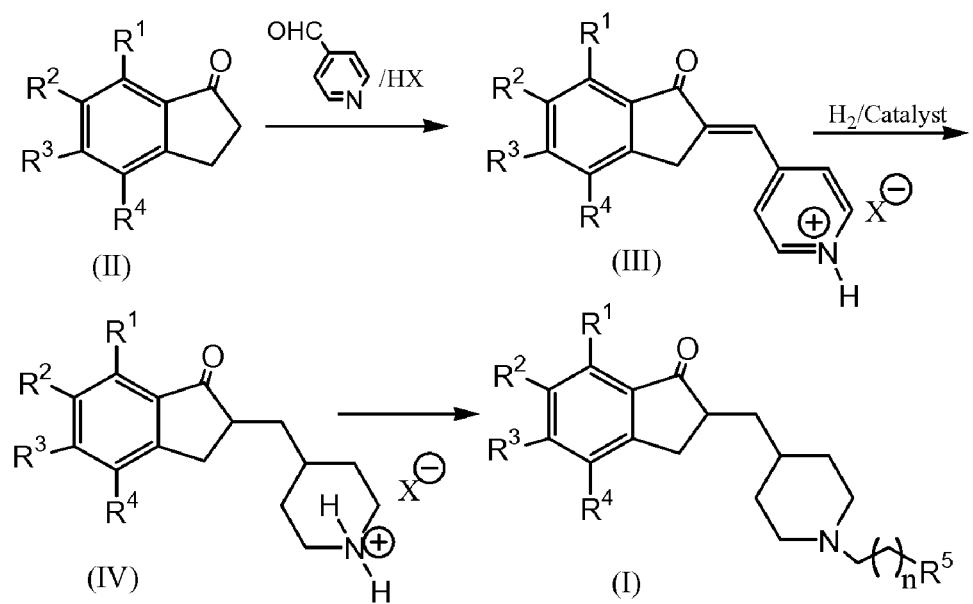
FIG. 8 illustrates a process for the preparation of Donepezil according to this invention.

2,3-dihydro-5,6-dimethoxy-2-((pyridin-4-yl)methylene)inden-1-one p-toluenesulfonic acid salt 0.96 g of 5,6-dimethoxy-1-indanone, and 0.75 g 4-pyridyl formaldehyde were added to a three-neck round bottom flask equipped with a Dean-Stark trap and an electromagnetic stirrer. 100 ml toluene was then added. Stirring continued until the reactants were dissolved. Then, 0.95 g of p-toluenesulfonic acid was added. The reaction was then carried out by refluxing for 12 hrs. After cooling, a solid was formed. The resultant solid was filtered off with suction affording 2.141 g of a yellow solid compound. The yield was 94%. 20 mL of anhydrous ethanol were added to the product, and the slurry was brought under reflux in ethanol for 30 minutes. After cooling at 5° C. for 2 hours, the resulting precipitate was filtered off with suction and after washing with 5 ml cold anhydrous ethanol and drying, 1.98 g of the title product were obtained. The melting point range was from 209-212° C. $^1$H NMR (DMSO-$d_6$): 8.95 (d, 2H, J=6.0 Hz), 8.23 (d, 2H, J=6.0 Hz), 7.56 (s, 1H), 7.48 (d, 2H, J=8.0 Hz), 7.27 (s, 1H), 7.22 (s, 1H), 7.12 (d, 2H, J=8.0 Hz), 4.15 (s, 2H), 3.93 (s, 3H), 3.85 (s, 3H), 2.29 (s, 3H).

Example 2

2,3-dihydro-5,6-dimethoxy-2-((piperidin-4-yl)methyl)inden-1-one p-toluenesulfonic acid salt 0.402 g of 2,3-dihydro-5,6-dimethoxy-2-((pyridin-4-yl) methylene)inden-1-one p-toluenesulfonic salt were dissolved in 30 mL of methanol and 33 milligram of $PtO_2$ were added. Stirring continued at room temperature, with $H_2$ being supplied at 1 atmosphere for 7 hours. Solids filtered off with suction and washed with 5 ml anhydrous methanol. After concentrating the filtrate solid was obtained. To the solid 15 mL of anhydrous isopropanol was added. The mixture was heated to dissolve solids and then cooled to 0° C. overnight. The formed precipitate was filtered off with suction to afford 0.34 g of white crystalline solid. The melting point 191-192° C. After drying, additional 46 milligrams of solid were obtained. Liquid chromatography analysis showed product of 97% purity. A total of 0.386 g of the expected product was obtained at a yield of 94%. $^1$H NMR (DMSO-$d_6$): 8.42 (br s, 1H), 8.18 (br s, 1H), 7.47 (d, 2H, J=8.0 Hz), 7.12 (d, 2H, J=8.0 Hz), 7.11 (s, 1H), 7.06 (s, 1H), 3.87 (s, 3H), 3.79 (s, 3H), 3.20-3.38 (m, 3H), 2.82-2.95 (m, 2H), 2.60-2.75 (m, 2H), 2.29 (s, 3H), 1.85-1.95 (m, 1H), 1.65-1.85 (m, 3H), 1.20-1.40 (m, 3H).

Example 3

Synthesis of Donepezil (Method A)

0.18 g of 2,3-dihydro-5,6-dimethoxy-2-((piperidin-4-yl) methyl)inden-1-one p-toluenesulfonic acid salt were dissolved in 10 mL of dry N,N'-dimethylformamide. 0.073 g of benzyl bromide and 0.3 g of potassium carbonate were added thereto. The resulted mixture was stirred until the reaction completed. Then 60 mL of water were added and the solution was extracted with 4×30 mL of ethyl acetate. The extracts were combined, washed with 15 mL of $Na_2CO_3$ solution and with 15 mL NaCl solution, and dried over anhydrous $MgSO_4$. Drying agent was then filtered off. The solvent was removed in vacuo yielding 0.141 g of product, 96% yield. $^1$H NMR (CDCl$_3$), 7.15-7.35 (m, 5H), 7.09 (s, 1H), 6.78 (s, 1H), 3.89 (s, 3H), 3.84 (s, 3H), 3.48 (s, 2H), 3.17 (dd, 1H, J=8.0 Hz, J=17.6 Hz), 2.82-2.92 (m, 2H), 2.58-2.74 (m, 2H), 1.80-2.03 (m, 3H), 1.57-1.76 (m, 2H), 1.40-1.56 (m, 1H), 1.18-1.40 (m, 3H).

Example 4

2-((1-(3-fluorobenzyl)piperidin-4-yl)methyl)-2,3-dihydro-5,6-dimethoxyinden-1-one, was prepared according to Example 3 by replacing benzyl bromide with m-fluorobenzyl bromide.

Example 5

2,3-dihydro-5,6-dimethoxy-2-((pyridin-4-yl)methyl) inden-1-one 1.80 g of 2,3-dihydro-5,6-dimethoxy-2-((pyridin-4-yl)methylene)inden-1-one and 40 milligrams of $PtO_2$ were added to 15 mL glacial acetic acid. The reaction mixture was stirred at 80° C., with $H_2$ being supplied at 1 atmosphere for 6 hours. Solids were filtered off. The filtrate was concentrated. 30 mL of $Na_2CO_3$ aqueous solution were added thereto. The resulted mixture was extracted with of chloroform (5×20 mL). The extracts were combined, washed with brine, and dried over anhydrous $MgSO_4$. The drying agent was then filtered off. Solvent was removed in vacuo to give crude product. Purification of crude product by silica gel column chromatography ($CHCl_3/CH_3OH$ 95/5) afforded 0.63 g of white crystalline compound. The yield was 35%. $^1H$ NMR ($CDCl_3$): 8.53 (brs, 2H), 7.15-7.25 (m, 3H), 6.82 (s, 1H), 3.95 (s, 3H), 3.92 (s, 3H), 3.35 (dd, 1H, J=4.4, 14.0 Hz), 3.12 (dd, 1H, J=7.6, 16.8 Hz), 2.95-3.05 (m, 1H), 2.65-2.75 (m, 2H).

Example 6

2,3-dihydro-5,6-dimethoxy-2-((piperidin-4-yl)methyl)inden-1-one p-toluenesulfonic acid salt 0.60 g of 2,3-dihydro-5,6-dimethoxy-2-((pyridin-4-yl)methyl)inden-1-one, and 0.36 g p-toluenesulfonic acid salt were added to 30 mL of anhydrous methanol. 60 milligrams of $PtO_2$ were added. The reaction mixture was stirred at room temperature, with $H_2$ being added at 1 atmosphere for 6 hours. Solids were filtered off. The filtrate was concentrated and dried in vacuo to afford 1.05 g of foam with 100% yield. Liquid chromatography analysis of this product showed 97% purity.

Example 7

Synthesis of Donepezil (Method B)

0.22 g of 2,3-dihydro-5,6-dimethoxy-2-((piperidin-4-yl)methyl)inden-1-one p-toluenesulfonic acid salt, and 0.10 g of sodium acetate were added to 60 mL of anhydrous methanol. 100 milligrams of 10% Pd/C were also added. The reaction mixture was stirred at room temperature with $H_2$ being supplied at 1 atmosphere for 10 hours. 55 milligrams of benzaldehyde were added in equal portions at 0 hrs, 2 hrs, 4 hrs, 6 hrs and 8 hrs. Solids were filtered off. The filtrate was concentrated. 30 mL of 5% aqueous $Na_2CO_3$ solution were added, and the resulting mixture was extracted with 3×30 mL of ethyl acetate. The extracts were combined, washed with 15 mL of aqueous $Na_2CO_3$ solution and 15 mL of aqueous NaCl solution, and dried over anhydrous $MgSO_4$. After solids were filtered off, solvent was removed in vacuo to afford 0.67 g of product as oil. Purification on silica gel column chromatography afforded 0.11 g of title compound in 62% yield.

The invention claimed is:

1. A process for producing a compound of formula (I),

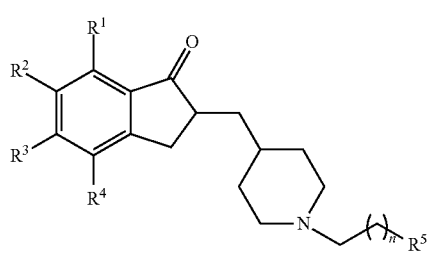

(I)

wherein $R^1$ and $R^4$ independently represent H, $R^2$ and $R^3$ independently represent H, F, an alkyl having from 1 to 4 carbon atoms, or an alkoxy having from 1 to 4 carbon atoms; $R^5$ represents a phenyl or a substituted phenyl; and n is 0, wherein the process comprises:

a) a reaction of 4-pyridinecarboxaldehyde with a compound of formula (II) in refluxing toluene or benzene to form, in the presence of a stoichiometric amount or a greater than a stoichiometric amount of a strong acid selected from an alkyl sulfonic acid, benzene sulfonic acid, or a substituted benzene sulfonic acid, a compound of the formula (III);

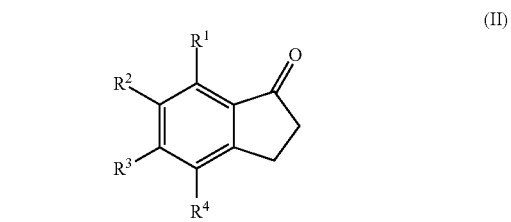

(II)

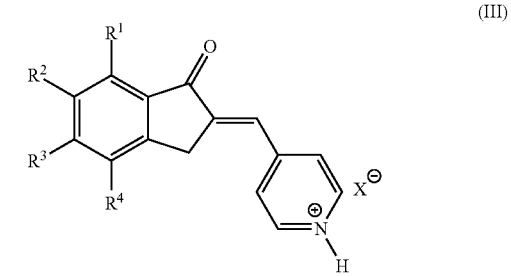

(III)

b) a catalytic hydrogenation of a compound of formula (III) or the compound of formula (V) in a solvent selected from water, an alcohol, an ether, an ester, or an organic acid, at a temperature of between about 0° C. and about 150° C., in the presence of a catalyst selected from platinum, palladium, nickel, ruthenium, or salts or oxides thereof, and at a pressure of between about 1 atmosphere and about 100 atmospheres of $H_2$ to yield a compound of formula (IV); and

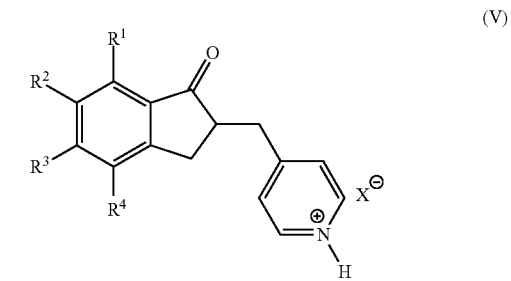

(V)

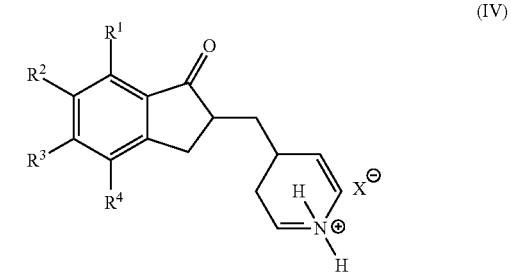

(IV)

c) an N-alkylation reaction of a compound of formula (IV) with a compound of formula $Y—(CH_2)_{n+1}R^5$, wherein Y represents a chlorine atom, a bromine atom, or an iodine atom, $R^5$ represents a phenyl or a substituted phenyl, and n is 0; in the presence of base at a temperature of from about 0° C. to about 150° C. to yield a compound of formula (I);
wherein $X^-$ is an alkyl sulfonate, benzene sulfonate, or a substituted benzene sulfonate.

2. The process of claim 1 wherein a compound of formula (IV) is produced by the catalytic hydrogenation of a compound of formula (III).

3. The process of claim 1, wherein a compound of formula (IV) is produced by catalytic hydrogenation of a compound of formula (V).

4. The process of claim 1, wherein $R^1$ represents hydrogen; $R^2$ represents a methoxy; $R^3$ represents a methoxy; $R^4$ represents hydrogen; $R^5$ represents a phenyl or a 3-fluorophenyl; n is 0; said strong acid is selected from methyl sulfonic acid, benzene sulfonic acid, or p-toluenesulfonic acid; and Y represents a chlorine, a bromine, or an iodine.

5. The process of claim 1, wherein within said compound of formula (III) $R^1$ represents hydrogen, $R^2$ represents methoxy, $R^3$ represents methoxy, $R^4$ represents hydrogen; said strong acid is selected from methyl sulfonic acid, benzene sulfonic acid, or p-toluenesulfonic acid, wherein said compound of formula (IV) is produced from a compound of formula (III) by catalytic hydrogenation, wherein the catalyst is platinum, palladium, nickel, ruthenium, or salts or oxides thereof.

6. The process of claim 2, wherein within said compound of formula (III) $R^1$ represents hydrogen, $R^2$ represents methoxy, $R^3$ represents methoxy, $R^4$ represents hydrogen; said strong acid is selected from methyl sulfonic acid, benzene sulfonic acid, or p-toluenesulfonic acid, wherein said compound of formula (IV) is produced from a compound of formula (III) by catalytic hydrogenation, wherein the catalyst is platinum, palladium, nickel, ruthenium, or salts or oxides thereof.

7. The process of claim 3, wherein within said compound of formula (V) $R^1$ represents hydrogen, $R^2$ represents methoxy, $R^3$ represents methoxy, $R^4$ represents hydrogen; said strong acid is selected from methyl sulfonic acid, benzene sulfonic acid, or p-toluenesulfonic acid, wherein said compound of formula (IV) is produced from a compound of formula (V) by catalytic hydrogenation, wherein the catalyst is platinum, palladium, nickel, ruthenium, or salts or oxides thereof.

8. The process of claim 1, wherein within said compound of formula (V) $R^1$ represents hydrogen, $R^2$ represents methoxy, $R^3$ represents methoxy, $R^4$ represents hydrogen; said strong acid is selected from methyl sulfonic acid, benzene sulfonic acid, or p-toluenesulfonic acid, wherein said compound of formula (IV) is produced from a compound of formula (V) by catalytic hydrogenation, wherein the catalyst is platinum, palladium, nickel, ruthenium, or salts or oxides thereof.

9. The process of claim 2, wherein within said compound of formula (III) $R^1$ represents hydrogen, $R^2$ represents methoxy, $R^3$ represents methoxy, $R^4$ represents hydrogen; said strong acid is selected from methyl sulfonic acid, benzene sulfonic acid, or p-toluenesulfonic acid, wherein said compound of formula (IV) is produced from a compound of formula (III) by catalytic hydrogenation, wherein the catalyst is platinum, palladium, nickel, ruthenium, or salts or oxides thereof.

10. The process of claim 3, wherein within said compound of formula (V) $R^1$ represents hydrogen, $R^2$ represents methoxy, $R^3$ represents methoxy, $R^4$ represents hydrogen; said strong acid is selected from methyl sulfonic acid, benzene sulfonic acid, or p-toluenesulfonic acid, wherein said compound of formula (IV) is produced from a compound of formula (V) by catalytic hydrogenation, wherein the catalyst is platinum, palladium, nickel, ruthenium, or salts or oxides thereof.

11. The process of claim 1, wherein reacting 4-pyridinecarboxaldehyde with a compound of formula (II) in the presence of a stoichiometric amount or a greater than a stoichiometric amount of methyl sulfonic acid, benzene sulfonic acid, or p-toluenesulfonic acid yields a compound of formula (III), wherein $R^1$ represents hydrogen, $R^2$ represents methoxy, $R^3$ represents methoxy, and $R^4$ represents hydrogen.

12. A process for producing a compound of formula (I),

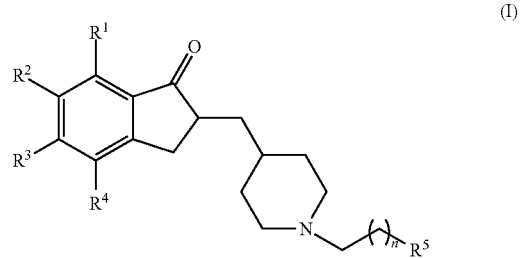

(I)

wherein $R^1$ and $R^4$ independently represent H, $R^2$ and $R^3$ independently represent H, F, an alkyl having from 1 to 4 carbon atoms, or an alkoxy having from 1 to 4 carbon atoms; $R^5$ represents a phenyl or a substituted phenyl; and n is 0, comprising:
a) a reaction of 4-pyridinecarboxaldehyde with a compound of formula (II) in refluxing toluene, in the presence of at least a stoichiometric amount of a strong acid selected from an alkyl sulfonic acid, benzene sulfonic acid, or a substituted benzene sulfonic acid to form a compound of formula (III);

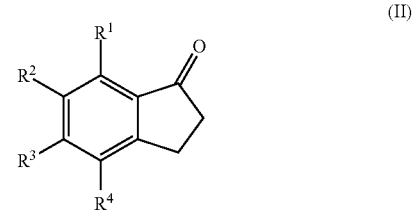

(II)

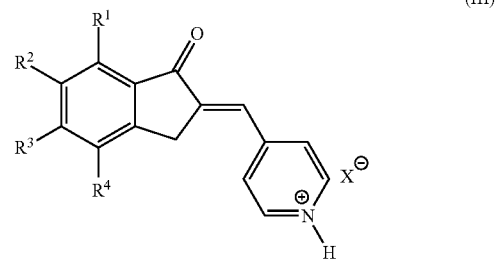

(III)

b) a catalytic hydrogenation of a compound of formula (III) or the compound of formula (V) in methanol, ethanol, and/or water; in the presence of Pd/C or $PtO_2$; at a temperature of between about 0° C. and about 150° C., and at a pressure of between about 1 atmosphere and about 100 atmospheres of $H_2$ to yield a compound of formula (IV); and

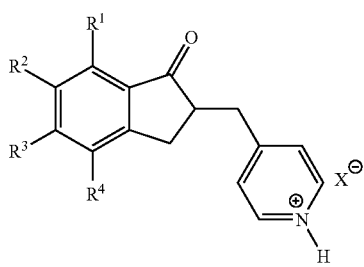

(V)

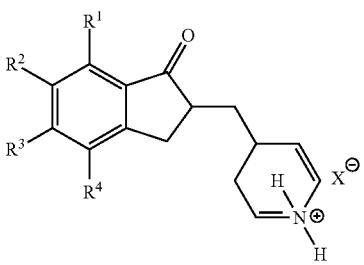

(IV)

c) a reaction of a compound of formula (IV) with a compound of formula OHC—$(CH_2)_nR^5$, wherein $R^5$ represents a phenyl or a substituted phenyl, and n is 0, and with $H_2$, in the presence of a base and Pd/C, at a temperature of from about 0° C. to about 150° C., to yield a compound of formula (I);

wherein $X^-$ is an alkyl sulfonate, benzene sulfonate, or a substituted benzene sulfonate.

13. A process for producing a compound of formula (I),

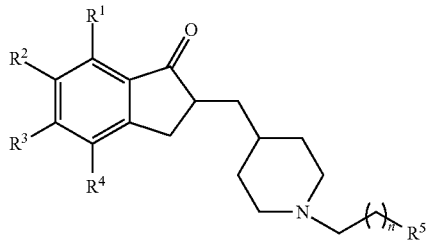

(I)

wherein $R^1$ and $R^4$ independently represent H, $R^2$ and $R^3$ independently represent H, F, an alkyl having from 1 to 4 carbon atoms, or an alkoxy having from 1 to 4 carbon atoms; $R^5$ represents a phenyl or a substituted phenyl; and n is 0, comprising:

a) a reaction of 4-pyridinecarboxaldehyde with a compound of formula (II) in refluxing toluene, in the presence of at least a stoichiometric amount of p-toluenesulfonic acid with respect to the compound of formula (II), to form a compound of formula (III);

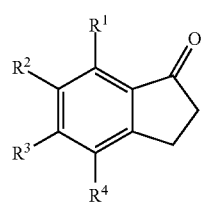

(II)

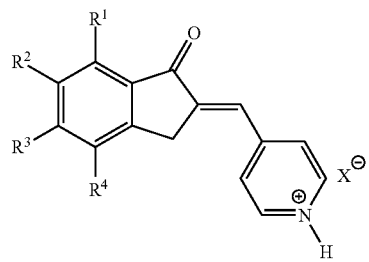

(III)

b) a catalytic hydrogenation of a compound of formula (III) or the compound of formula (V) in methanol and/or water with $H_2$ in the presence of Pd/C to yield a compound of formula (IV);

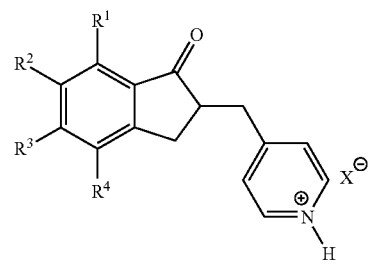

(V)

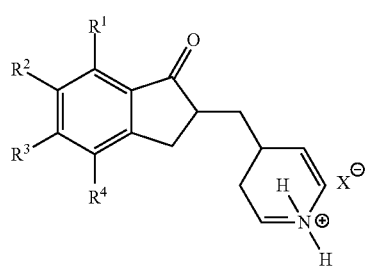

(IV)

c) a reaction of a compound of formula (IV) with a compound of formula OHC—$(CH_2)_nR^5$, wherein $R^5$ represents a phenyl or a substituted phenyl, and n is 0, and with $H_2$, in methanol, in the presence of Pd/C and a base, at a temperature of from about 0° C. to about 150° C., to yield a compound of formula (I);

wherein b) and c) are carried out in situ without purification of the compound of formula (IV); and $X^-$ is p-toluene sulfonate.

14. A process for producing a compound of formula (I),

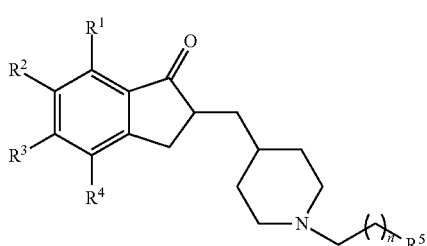

(I)

wherein $R^1$ and $R^4$ independently represent H, $R^2$ and $R^3$ independently represent H, F, an alkyl having from 1 to 4 carbon atoms, or an alkoxy having from 1 to 4 carbon atoms; $R^5$ represents a phenyl or a substituted phenyl; and n is 0, comprising the following steps:

a) a reaction of 4-pyridinecarboxaldehyde with a compound of formula (II) in refluxing toluene, in the presence of a stoichiometric amount of p-toluenesulfonic acid with respect to the compound of formula (II), to form a compound of formula (III)

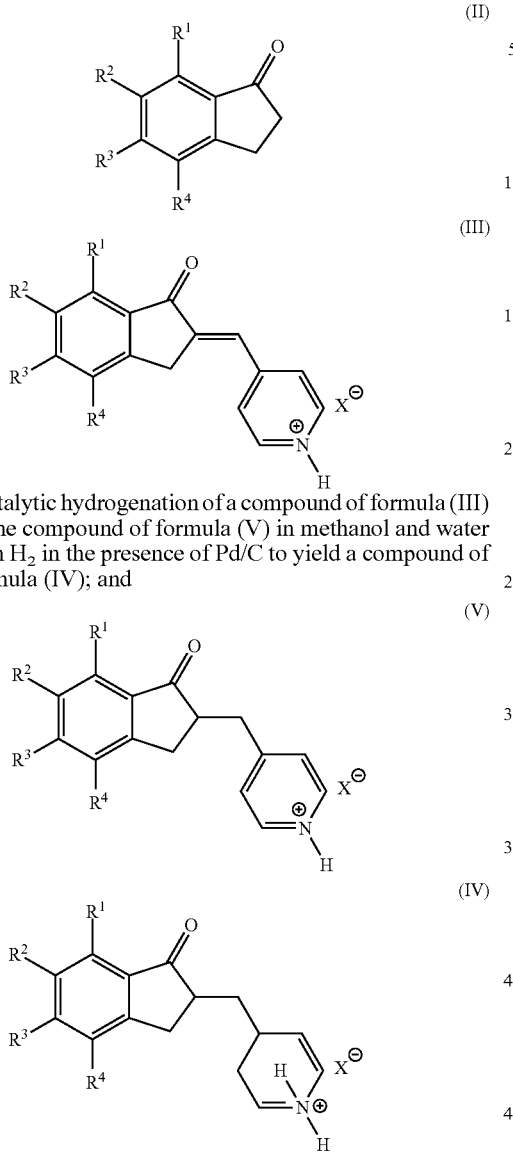

b) a catalytic hydrogenation of a compound of formula (III) or the compound of formula (V) in methanol and water with $H_2$ in the presence of Pd/C to yield a compound of formula (IV); and c) a reaction of a compound of formula (IV) with a compound of formula $OHC-(CH_2)_nR^5$, wherein $R^5$ represents a phenyl or a substituted phenyl, and n is 0, and with $H_2$, in methanol, in the presence of Pd/C and a base, at a temperature of from about 0° C. to about 150° C., to yield a compound of formula (I);

wherein b) and c) are carried out in situ without purification of the compound of formula (IV); and $X^-$ is p-toluene sulfonate.

15. The process of claim 14, wherein said compound of formula (IV) is produced by the catalytic hydrogenation of said compound of formula (III).

16. The process of claim 14, wherein $R^1$ represents hydrogen; $R^2$ represents a methoxy; $R^3$ represents a methoxy; $R^4$ represents hydrogen; and $R^5$ represents a phenyl or a 3-fluorophenyl.

17. The process of claim 14, wherein said compound of formula (IV) is produced from a compound of formula (III) by catalytic hydrogenation, wherein the catalyst is platinum, palladium, nickel, ruthenium, or salts or oxides thereof.

18. The process of claim 14, wherein said compound of formula (II) is 5,6-dimethoxy-1-indanone.

19. The process of claim 14, wherein steps (a)-(c) are carried out in succession and in the order listed.

20. The process of claim 14, wherein in step (a) the reaction of 4-pyridinecarboxaldehyde with a compound of formula (II) in refluxing toluene is carried out in the presence of a greater than a stoichiometric amount of p-toluenesulfonic acid with respect to the compound of formula (II).

21. A process for producing a compound of formula (I),

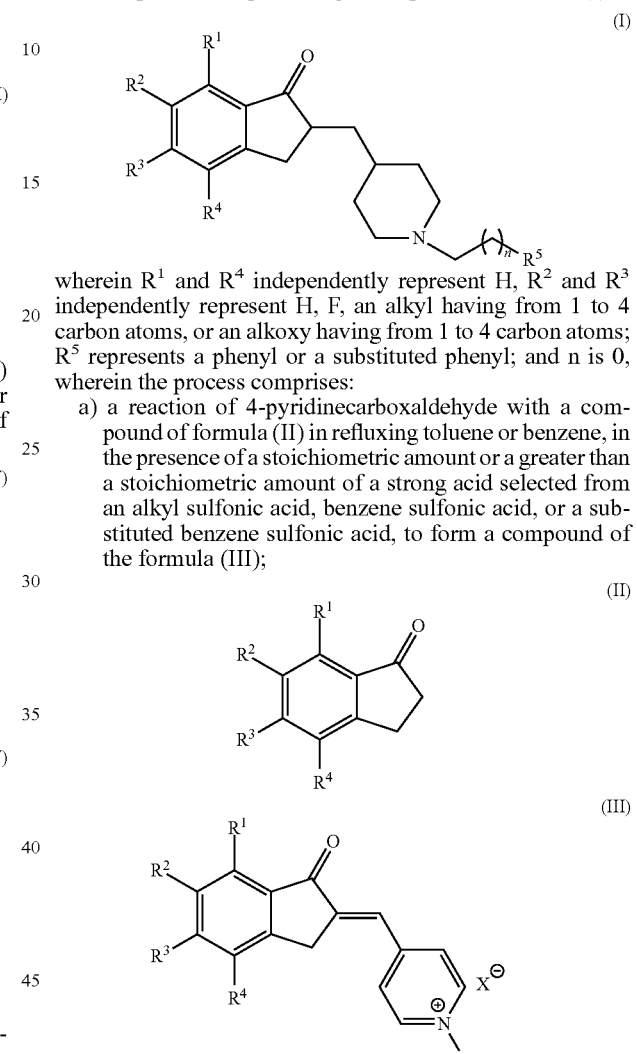

wherein $R^1$ and $R^4$ independently represent H, $R^2$ and $R^3$ independently represent H, F, an alkyl having from 1 to 4 carbon atoms, or an alkoxy having from 1 to 4 carbon atoms; $R^5$ represents a phenyl or a substituted phenyl; and n is 0, wherein the process comprises:

a) a reaction of 4-pyridinecarboxaldehyde with a compound of formula (II) in refluxing toluene or benzene, in the presence of a stoichiometric amount or a greater than a stoichiometric amount of a strong acid selected from an alkyl sulfonic acid, benzene sulfonic acid, or a substituted benzene sulfonic acid, to form a compound of the formula (III);

b) a catalytic hydrogenation of a compound of formula (III) in a solvent selected from water, an alcohol, an ether, an ester, or an organic acid, in the presence of a catalyst selected from platinum, palladium, nickel, ruthenium, or salts or oxides thereof, at room temperature and at a pressure of 1 atmosphere of $H_2$ to yield a compound of formula (IV); and -continued (IV)

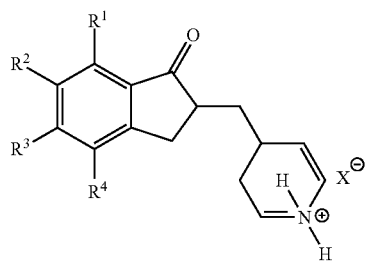

c) an N-alkylation reaction of a compound of formula (IV) with a compound of formula Y—(CH$_2$)$_{n+1}$R$^5$, wherein Y represents a chlorine atom, a bromine atom, or an iodine atom; in the presence of base at a temperature of from about 0° C. to about 150° C. to yield a compound of formula (I);

wherein X is an alkyl sulfonate, benzene sulfonate, or a substituted benzene sulfonate.

* * * * *